(12) United States Patent
Roncone (10) Patent No.: US 8,568,139 B2
(45) Date of Patent: Oct. 29, 2013

(54) ORTHODONTIC BRACKET

(76) Inventor: Ronald M Roncone, Rancho Santa Fe, CA (US)

( * ) Notice: Subject to any disclaimer, the term of this patent is extended or adjusted under 35 U.S.C. 154(b) by 0 days.

(21) Appl. No.: 13/304,220

(22) Filed: Nov. 23, 2011

(65) Prior Publication Data

US 2013/0130189 A1 May 23, 2013

(51) Int. Cl.
*A61C 7/14* (2006.01)
(52) U.S. Cl.
USPC .......................................................... 433/11
(58) Field of Classification Search
USPC .................................................. 433/8–17
See application file for complete search history.

(56) References Cited

U.S. PATENT DOCUMENTS

| | | | |
|---|---|---|---|
| 3,052,028 A | 9/1962 | Wallshein | |
| 3,772,787 A | 11/1973 | Hanson | |
| 4,248,588 A | 2/1981 | Hanson | |
| 4,492,573 A | 1/1985 | Hanson | |
| 4,698,017 A | 10/1987 | Hanson | |
| 4,712,999 A | 12/1987 | Rosenberg | |
| 5,275,557 A | 1/1994 | Damon | |
| 5,429,500 A | 7/1995 | Damon | |
| 5,439,378 A | 8/1995 | Damon | |
| 5,466,151 A | 11/1995 | Damon | |
| 5,474,445 A | 12/1995 | Voudouris | |
| 5,586,882 A | 12/1996 | Hanson | |
| 5,630,715 A | 5/1997 | Voudouris | |
| 5,685,711 A | 11/1997 | Hanson | |
| 5,857,849 A | 1/1999 | Kurz | |
| 5,906,486 A | 5/1999 | Hanson | |
| 5,971,753 A * | 10/1999 | Heiser | 433/11 |
| 6,071,118 A * | 6/2000 | Damon | 433/9 |
| 6,071,119 A * | 6/2000 | Christoff et al. | 433/14 |
| 6,257,883 B1 | 7/2001 | Voudouris | |
| 6,368,105 B1 | 4/2002 | Voudouris et al. | |
| 6,632,088 B2 | 10/2003 | Voudouris | |
| 7,063,531 B2 * | 6/2006 | Maijer et al. | 433/11 |
| 7,104,791 B2 | 9/2006 | Hanson | |
| 7,214,057 B2 | 5/2007 | Voudouris | |
| 7,306,457 B2 | 12/2007 | Vigolo | |
| 7,621,743 B2 * | 11/2009 | Bathen et al. | 433/10 |
| 7,686,613 B2 | 3/2010 | Pospisil et al. | |
| 7,704,072 B2 | 4/2010 | Damon | |
| 7,963,767 B2 | 6/2011 | Lewis et al. | |
| 7,963,768 B2 | 6/2011 | Hilliard | |
| 7,967,603 B2 | 6/2011 | Heiser | |
| 2002/0034715 A1 * | 3/2002 | Hanson | 433/11 |
| 2004/0072119 A1 | 4/2004 | Voudouris | |
| 2006/0051721 A1 | 3/2006 | Lluch | |
| 2007/0160949 A1 | 7/2007 | Voudouris | |
| 2007/0243497 A1 | 10/2007 | Voudouris | |

* cited by examiner

*Primary Examiner* — Cris L Rodriguez
*Assistant Examiner* — Matthew Seward
(74) *Attorney, Agent, or Firm* — The Maxham Firm (57) ABSTRACT

An orthodontic bracket which can be selectively active or passive, and can be active or passive on one tooth and can be independently active or passive on adjacent or any other tooth. The bracket includes a body having a groove for receiving an archwire, a slide for moving from an open position to a closed position to thereby capture the archwire, and a spring slidably engageable in the slide in either a passive or an active position. When in the active position the spring bears on the archwire. A method of using this orthodontic bracket includes acts or steps which are made up of mounting the body to a patient's tooth with the slide in the open position, inserting an archwire into the groove in the body and closing the slide to secure the archwire in the groove. The spring can be in the passive or in the active position.

10 Claims, 10 Drawing Sheets

ORTHODONTIC BRACKET

FIELD OF THE BRACKET

This apparatus relates generally to orthodontic brackets and, more particularly, to such a bracket that can function as an active or a passive bracket, as chosen by the orthodontist at any time during treatment.

DISCUSSION OF PRIOR ART

When the alignment, or position, or both, of a person's teeth or tooth is being adjusted, brackets are affixed to the teeth to be adjusted and wires are typically connected between two or more such brackets. Typically, after brackets are placed on the patient's teeth, a wire is laterally inserted into each bracket and tension is applied to the wire between each two adjacent teeth.

The notion of a "passive" bracket was introduced approximately 10 years ago. The implication was that if an external force such as a steel tie or an elastomeric or a spring was present in a bracket system, that bracket was "active." Further implied was that this system created friction which was in some way harmful in the efficient movement of teeth. The orthodontic literature does not support either of these contentions. Firstly, if a bracket/wire system was truly passive, no tooth movement could take place. In order for tooth movement to occur the wire must actively engage the bracket in some way. Secondly, studies have shown that tooth movement does not occur any more rapidly with passive brackets than with active brackets. This distinction is mentioned only for reasons of explaining the differences in these types of self-ligating brackets (SLB). Orthodontists will continue to favor one type or another for their own clinical reasons

SUMMARY OF EMBODIMENTS OF THE INVENTION

The present orthodontic bracket offers improvements over the currently available orthodontic brackets.

The bracket can function in either a passive or an active manner. Each bracket of a mounted set of brackets can be selectively active or passive in function. That is, an active spring in the bracket can be engaged for the bracket to function in an active mode, and it can be disengaged for the bracket to function in the passive mode.

The bracket is configured for vertical wire insertion, thereby permitting easy access for the wire to be inserted into or removed from the brackets on either or both the upper and lower arches.

BRIEF DESCRIPTION OF THE DRAWING

The brackets are described in the following detailed description and their structure and function will be readily perceived with reference to the accompanying drawing, in which.

DETAILED DESCRIPTION OF EMBODIMENTS OF THE INVENTION

Figure 1A:
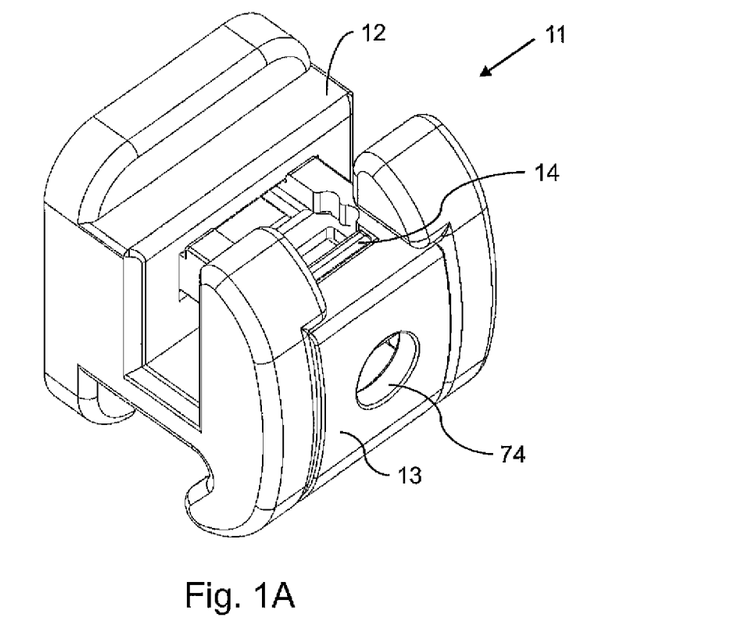
FIG. 1A is a perspective view of an embodiment of the bracket according to the invention in a closed position.
Figure 1B:
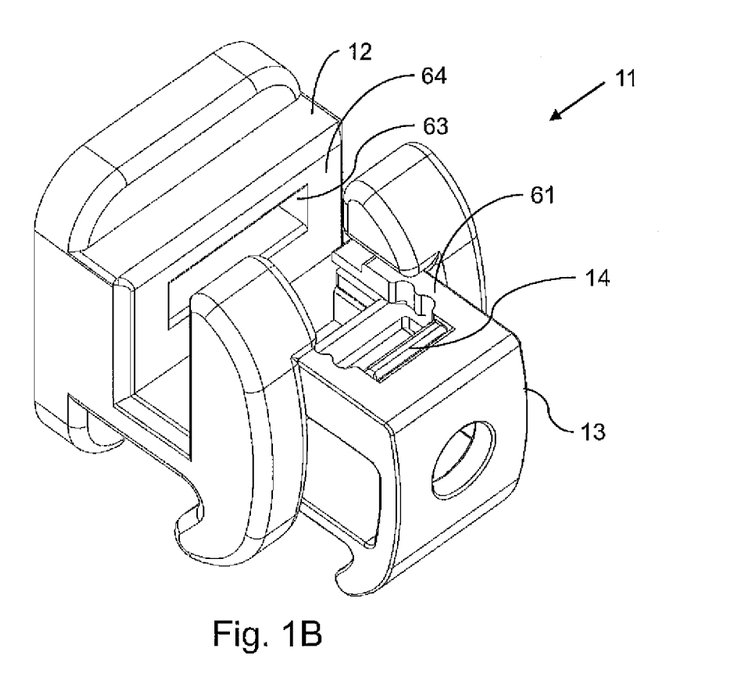
FIG. 1B is a perspective view of the bracket of FIG. 1A in an open position.
Figure 2:
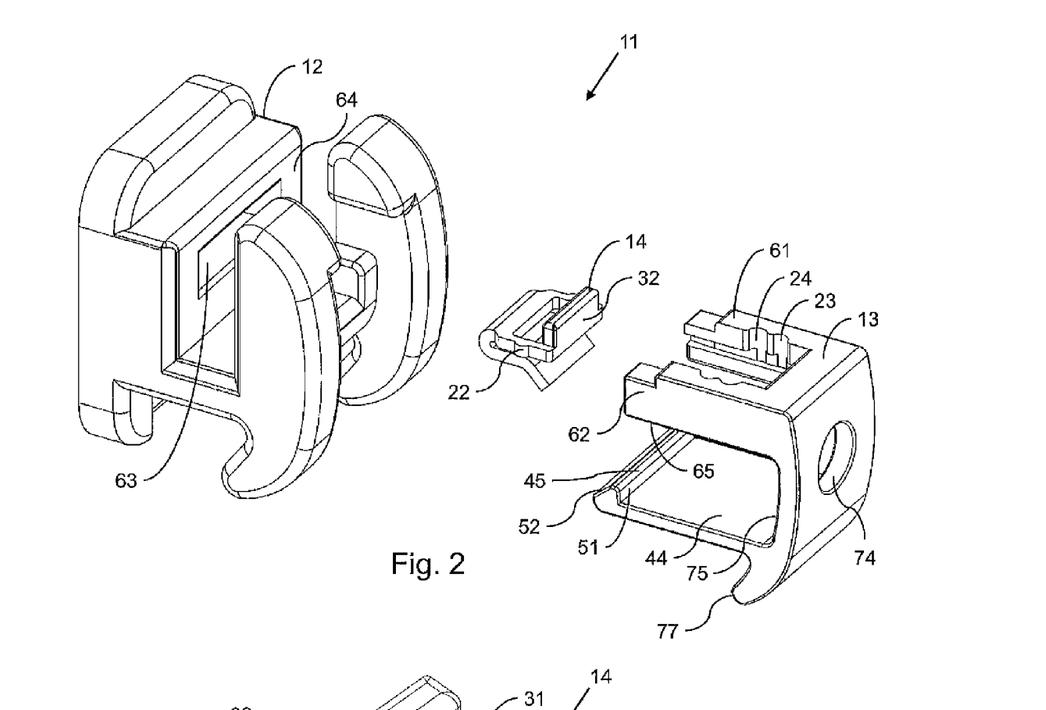
FIG. 2 is an exploded perspective view of the bracket of FIG. 1.

With reference now to the drawing, and more particularly to FIGS. 1A, 1B, and 2, an embodiment of the orthodontic bracket will be generally described. Orthodontic bracket 11, as shown in this embodiment, has three elements: body 12, slide 13, and activation spring 14. FIG. 1A shows the bracket in its closed position, FIG. 1B shows the bracket open, and FIG. 2 clearly depicts the three elements in an exploded perspective view.

Figure 3A:
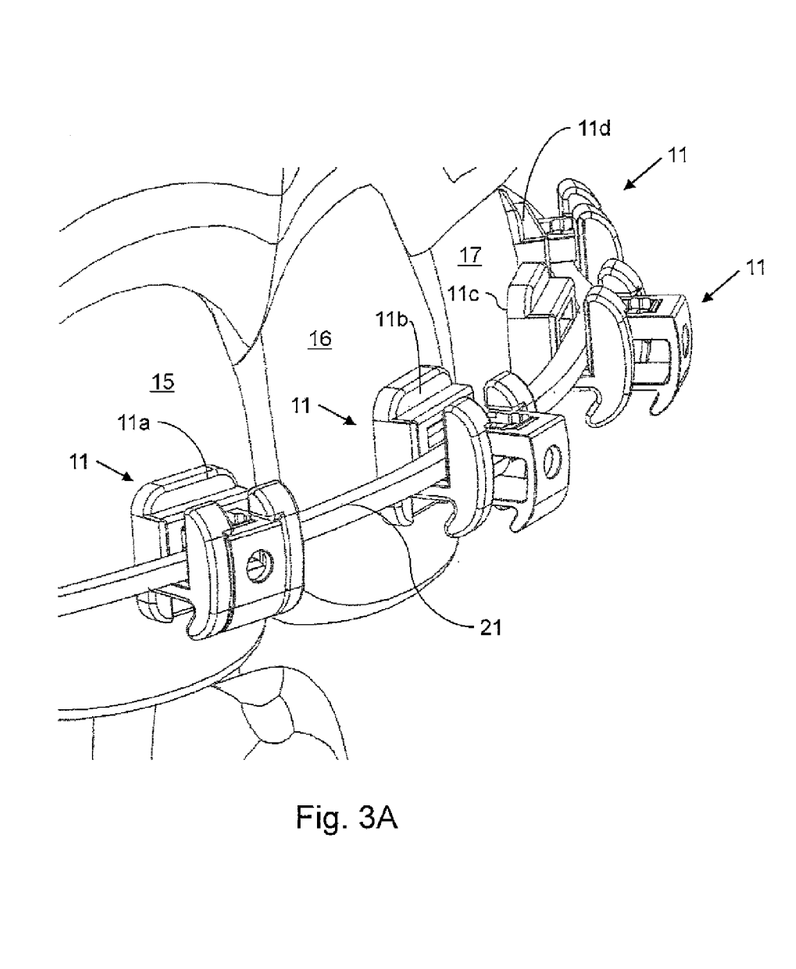
FIG. 3A is a perspective view of a portion of a person's mouth showing several upper teeth with the brackets thereon and with an exemplary archwire in position.
Figure 3B:
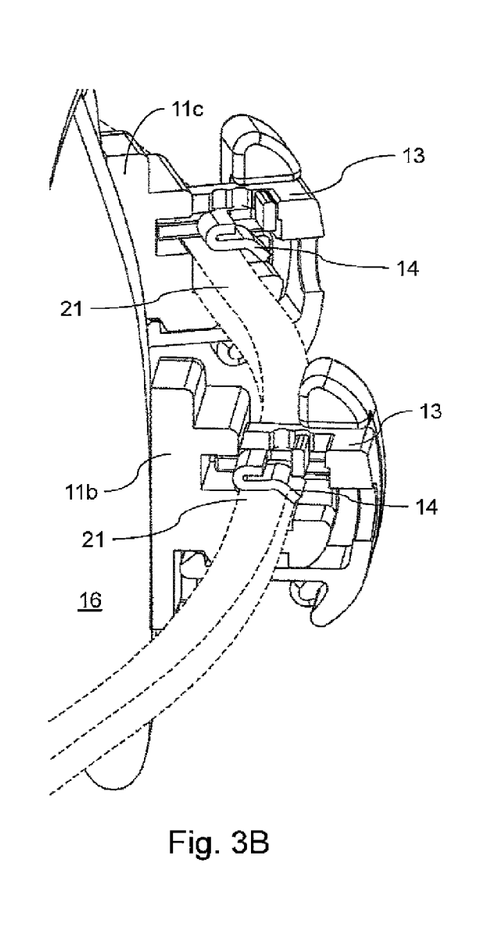
FIG. 3B is a somewhat enlarged fragmentary perspective view of the two brackets in situ, one in a passive condition and the other in an activated condition.

The bracket and its manner of use will now be described in detail. A partial mouth view is shown in FIGS. 3A and 3B. Each bracket 11 is affixed to teeth 15, 16, 17, as seen in FIG. 3A. Archwire 21 is secured in bracket 11a on tooth 15 and in bracket 11d (the tooth to which bracket lid is mounted is not visible in this figure). The archwire is inserted into brackets 11b and 11c, both of which are shown in the open position.

FIG. 3B is an enlarged view of brackets 11b and 11c, with both brackets now in the closed position, showing archwire 21 (in dotted lines) secured in both brackets. In bracket 11c, spring 14 is in position one, that is, in a passive condition. Bracket 11b has spring 14 in an activated condition, or position two. Positions one and two of spring 14 are shown in top sectional views, FIGS. 4A and 4B, respectively. Projections 22 on either side of the spring are sized to selectively be seated in detents or grooves 23 and 24 in slide 13. When spring 14 is in position one, the passive position, projections 22 reside in detents 23. When the spring is in position two, the activated position, it is moved toward tooth engaging face 12a of body 12 and projections 22 reside in detents 24. Spring 14 is made of material that is relatively rigid and can be deflected to a relatively small degree. Specifically, opening 31 enables the sides of the spring to flex sufficiently so that a moderate force applied on bar 32 of the spring results in projection 22 being forced out of detent 23, whereupon it will be seated in detent 24 when the spring slides to the activated position. Thus, positions one and two are both stable positions of spring 14.

Figure 4A:
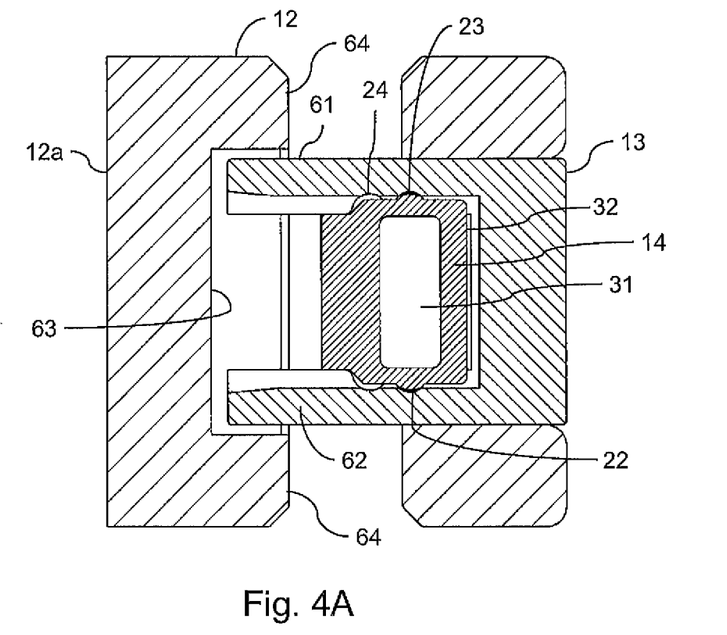
FIG. 4A is a top sectional view of the bracket of FIG. 1 in the passive condition.
Figure 4B:
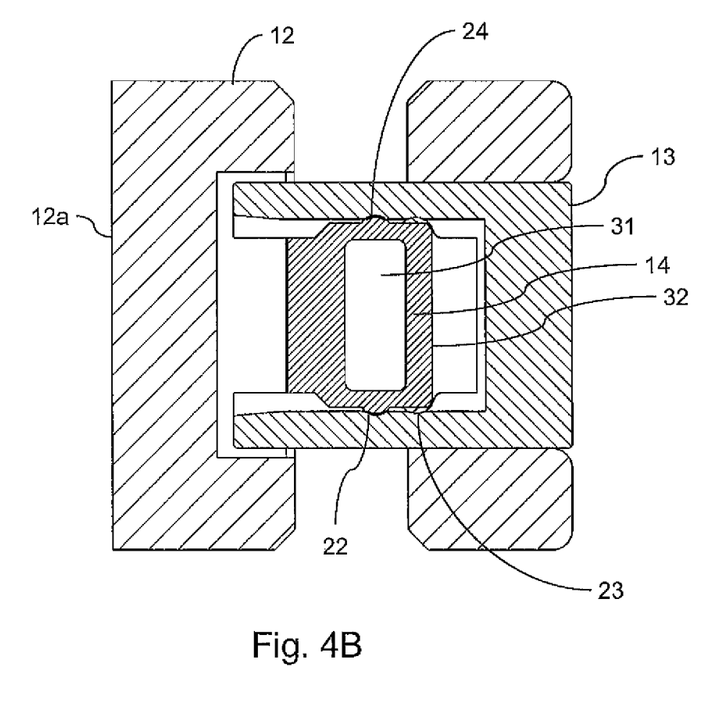
FIG. 4B is a top sectional view of the bracket of FIG. 1 in the activated condition.

A force applied to spring 14 in the opposite direction causes the spring to move away from tooth engaging face 12a.

Figure 5:
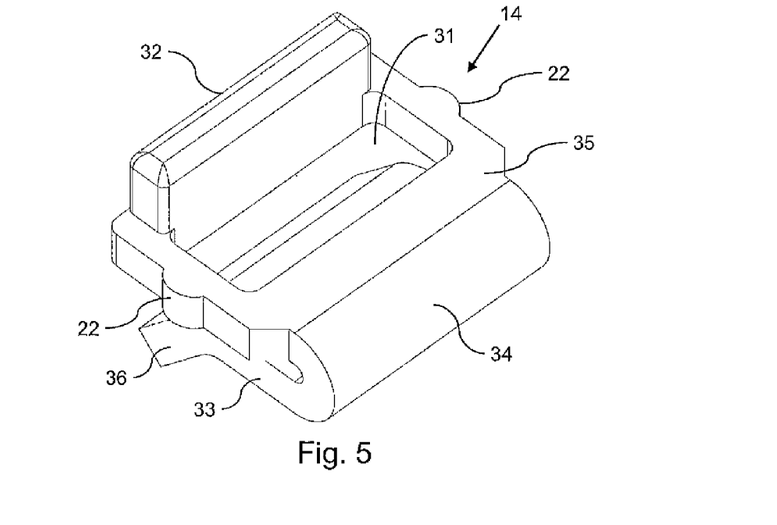
FIG. 5 is a greatly enlarged perspective view of the spring element of the bracket of FIGS. 1 and 2.

Spring 14 is shown in greater detail in FIG. 5. Arm 33 is connected through bend 34 and doubles back to be generally parallel with frame 35 when in the non-activated position. Activating tab 36 extends at an angle from arm 33 and is configured to engage the archwire for activation of the bracket, as will be discussed in detail below.

Figure 6:
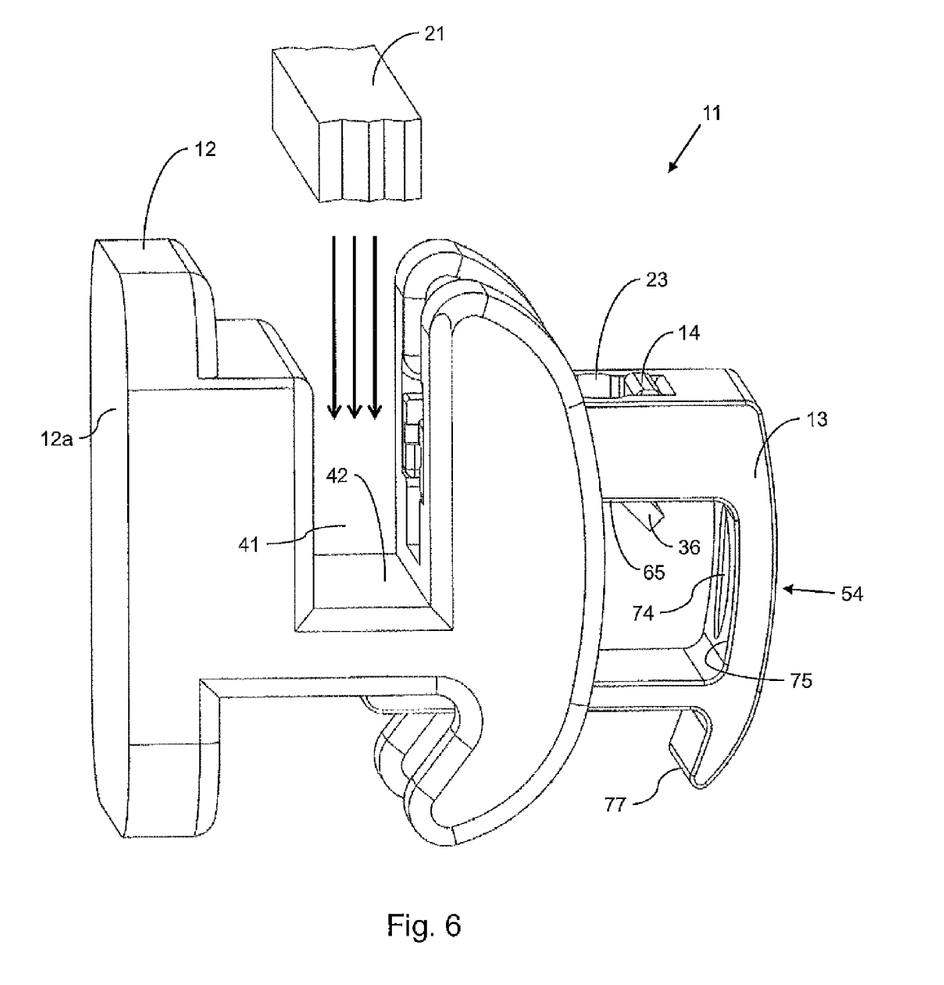
FIG. 6 is an enlarged perspective view of the bracket of FIG. 1 in an open position with an archwire segment poised for insertion.

Bracket 11 is shown in the open, pre-load position in FIG. 6. Archwire 21 is loaded from the top into groove 41 in body 12 and is seated on floor 42 of the body groove. To close the bracket, a force is applied to slide 13 in the direction of arrow 54 and the slide moves to the left in this figure, toward tooth engaging face 12a. When slide 13 is fully seated in body 12, archwire 21 is captured in groove 41, as will be detailed below.

Figures 7A, 7B, 7C:
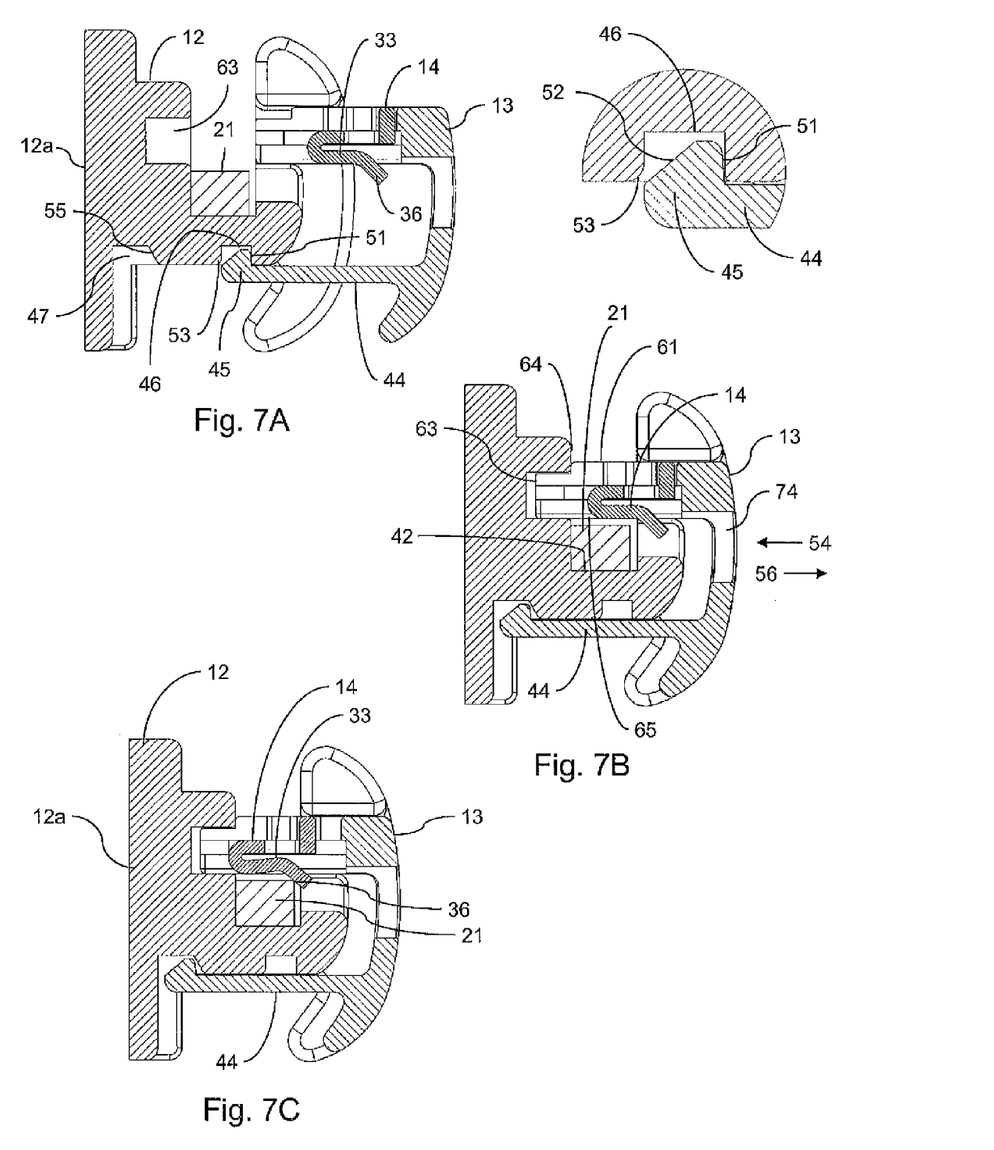
FIG. 7A is a sectional side view of the bracket of FIG. 1 in an open position and with an archwire in place.
FIG. 7B is a similar sectional view in a closed position with the spring in a passive condition.
FIG. 7C is a sectional perspective view similar to FIG. 7B in an active condition.

FIGS. 7A, 7B, and 7C show the bracket in several positions in the orthodontic procedure. In FIG. 7A, after archwire 21 is in position, the bracket is ready to perform its function. Face 12a on body 12 has been affixed to a patient's tooth. Arm 44 of slide 13 is formed with projection 45 which selectively resides in detents 46 and 47. The mutually engaging configurations of projection 45 and detents 46 and 47 are such that slide 13 is selectively movable and latched. When the bracket is open, as shown in FIG. 7A, projection 45 engages detent 46. Because outward facing surface 51 on projection 45 is at about a right angle with respect to the inner surface of arm 44, and detent 46 is formed as a generally square groove, slide 13 can be opened as shown in FIGS. 6 and 7A, but the engagement of projection 45 in detent 46 prevents the slide from becoming separated from the body. Angled surface 52 on the distal end of projection 45 enables the projection to ride over edge 53 of the outward facing surface of detent 46 when force is applied in the direction of arrow 54 (FIG. 7B). When slide 13 moves to the closed position (FIG. 7B), projection 45 engages detent 47. Because inward facing surface 55 is angled as shown, a force applied in the direction of arrow 56 causes projection 45 to ride up over the edge of detent 47 so that the slide can be moved to the right, as shown in FIG. 6, and thereby open the bracket. Because arm 44 of slide 13 is relatively rigid, projection 45 is in a stable position in either detent 46 or 47, and can flex sufficiently to enable the motion described above. While body 12 as shown has two detents, 46 and 47, there may be a reason to have another, or other intermediate detent or detents for an intermediate stable position of the slide. The bracket is thus not limited to any particular number of detents for positioning the slide with respect to the body.

With reference now to FIGS. 1B, 2, 4A, and 7B, inwardly projecting arms 61 and 62 of slide 13 extend into pocket 63 in outward facing wall 64 of body 12. As can be seen in FIG. 7B, archwire 21 is thereby confined in groove 41 between floor 42 and under surface 65 of arms 61, 62. In the passive position shown in FIG. 7B, spring 14 does not forcibly engage the archwire.

The bracket is shown activated in FIG. 7C. Spring 14 has been moved to the left and activating tab 36 is applying a force directly on the archwire, as is represented by the fact that arm 33 of the spring is angled upwardly and is not parallel with frame 35.

FIGS. 8A-8F are provided to indicate the different shapes and sizes of archwires that bracket 11 may accommodate. These cross sectional figures also variously show the bracket in passive and active conditions.

Figure 8A:
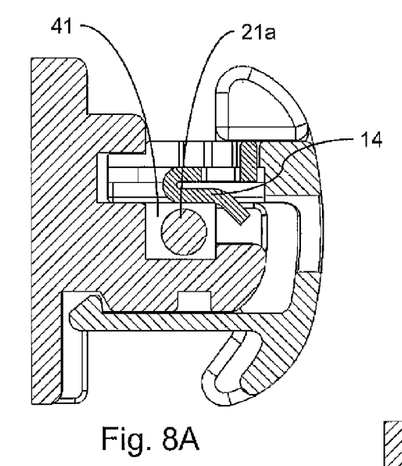
FIGS. 8A, 8B, 8C, 8D, 8E, and 8F are sectional side views of the bracket of FIG. 1 showing different sizes and shapes of wires that can be used with the bracket, variously in active and passive conditions.

In FIG. 8A, archwire 21a is round and does not completely fill groove 41. The bracket is shown closed with the spring in the passive position.

Figure 8B:
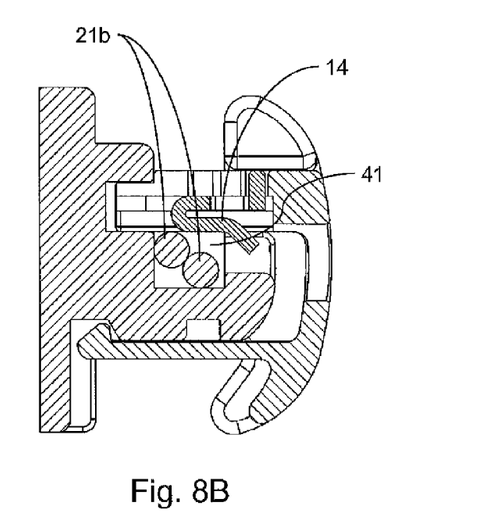
Figure 8C:
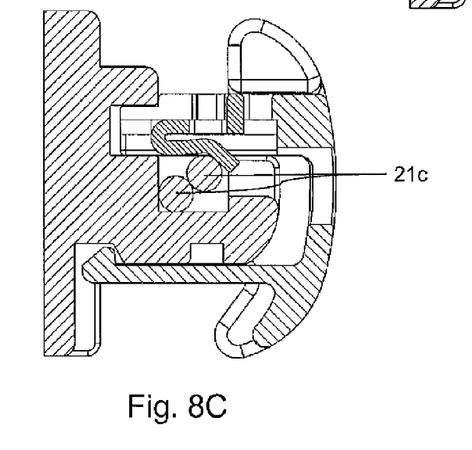

Two smaller wires 21b and 21c are shown in groove 41 in FIGS. 8B and 8C. Thus, the archwire is comprised of dual wires 21b and 21c. Spring 14 is again in the passive position in FIG. 8B. These two figures indicate that the two wires can have alterative orientations. In FIG. 8C, spring 14 has been moved to the left into the activated position.

In FIGS. 8A, 8B, and 8C, the archwires assume their place in slot 41 according to the "path of least resistance." During the initial round wire placement, activation of spring 14 may assist on alignment of the patient's tooth or teeth.

Figure 8D:
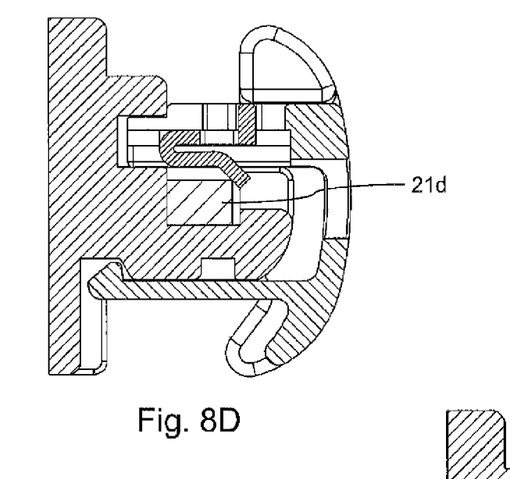
Figure 8E:
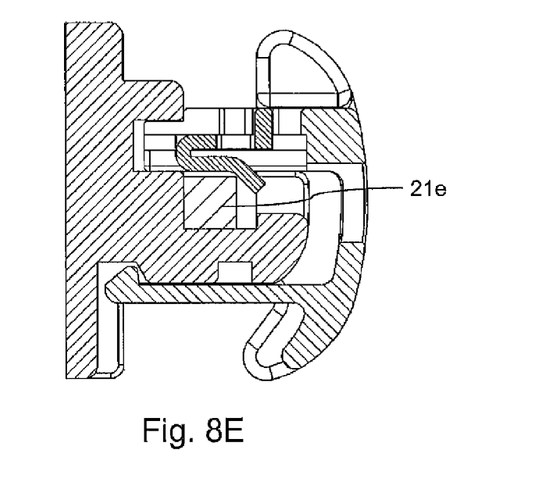
Figure 8F:
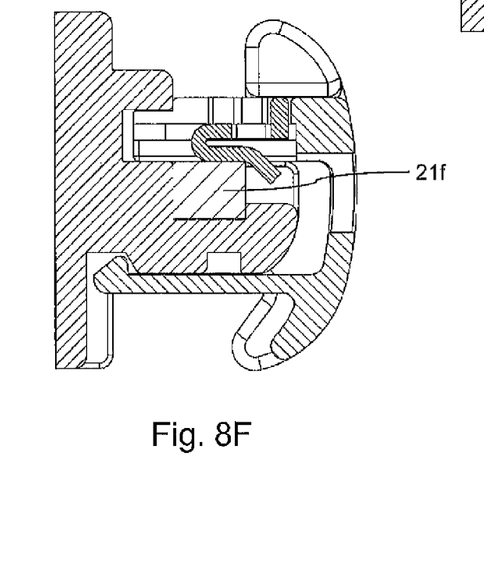

FIGS. 8D, 8E, and 8F show rectangular archwire 21d, square wire 21e, and larger rectangular wire 21f, respectively. The spring is in the activated position in FIGS. 8D and 8E. Larger rectangular archwire 21f is shown in FIG. 8F as substantially filling groove 41 and the bracket condition is passive.

For these rectangular archwires, when spring 14 is moved to the activated position it engages the upper right corner (as seen in FIGS. 8D, 8E, and 8F) of the wire and drives it into the lower left corner of slot 41. This allows, when desired, a significant torque to be applied, even with a relatively small rectangular wire. For example, slot 41 may be 0.022 inch deep and 0.028 inch wide, and a wire of size 0.017 inch by 0.025 inch will be subject to significant torque when the spring is moved to the activated position.

By way of example, slot 41 can have different sizes, such as 0.018 inch by 0.025 inch, in addition to the dimensions mentioned above. The larger wire in the vertical direction, the more spring 14 deflects from the horizontal, an example being shown in FIG. 8C.

In addition to the archwire sizes mentioned above, round wires may be 0.014-0.018 inch in diameter. These are standard archwire sizes but the bracket described herein can be used with any known archwire. Rectangular archwires may have a variety of sizes, such as 0.018 by 0.025 inch, 0.019 by 0.025 inch, 0.020 by 0.020 inch, 0.021 by 0.025 inch, or 0.022 by 0.028 inch. These are listed for purposes of example only and the bracket disclosed here is not limited to archwires of these dimensions.

A relatively simple instrument can be employed to move the spring to activate and deactivate the bracket. After the orthodontist has mounted brackets in the open position to the chosen teeth, the archwire is inserted from the top as shown in FIG. 6. Each bracket is then closed by pushing slide 13 inwardly, that is, toward the tooth, and the spring is moved to the activated position for each tooth, as desired. Alternatively, the spring can be moved to the activated position in the slide before the bracket is closed. In this case, after the archwire is inserted into groove 41 in the body, the slide, with the spring already moved to the activated position, is then moved to the closed position.

Figure 9A:
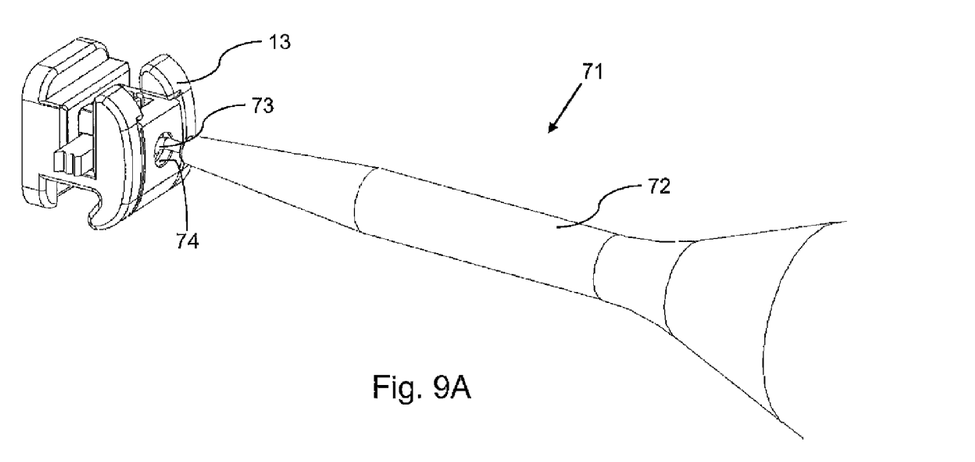
FIG. 9A is an example of an instrument that can be used to move the spring and to open the slide of the bracket of FIG. 1.
Figure 9B:
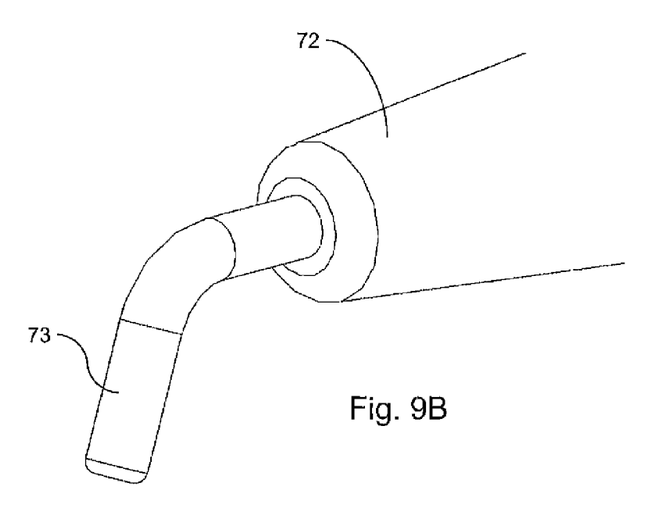
FIG. 9B is a greatly enlarged view of the tip of the instrument of FIG. 9A.

An example of an instrument that can function for more than one purpose is shown in FIG. 9. Instrument 71 has handle 72 and tip 73. For any bracket that is to be activated, the blunt end of instrument 71 is inserted through hole 74 in slide 13 to engage spring bar 32 and spring 14 is pushed from the passive position to the activated position (see FIGS. 7B and 7C). When it is desired to open the bracket to make adjustments or remove the archwire, hooked end 73 of instrument 71 is inserted through hole 74 and inside surface 75 of the slide is engaged. A pull on the so engaged instrument causes tooth 45 on slide arm 44 to slide out of detent 47 and slide 13 is moved to the open position, permitting removal or adjustment of the archwire. Slide tooth 45 then resides in detent 46, with the slide in a stable position with respect to body 12. Similarly, instrument 71 can move spring 14 from the active to the passive position by engaging the inside of bar 32, which is accessible as shown in FIG. 1, when the bracket is mounted on a tooth, whether in the closed or open position.

Instrument 71 may have a number of different shapes. It need only have an end which can push spring 14, and some kind of bend at the end to enable the slide to be engaged so it can be pulled to the open position.

Figure 10:
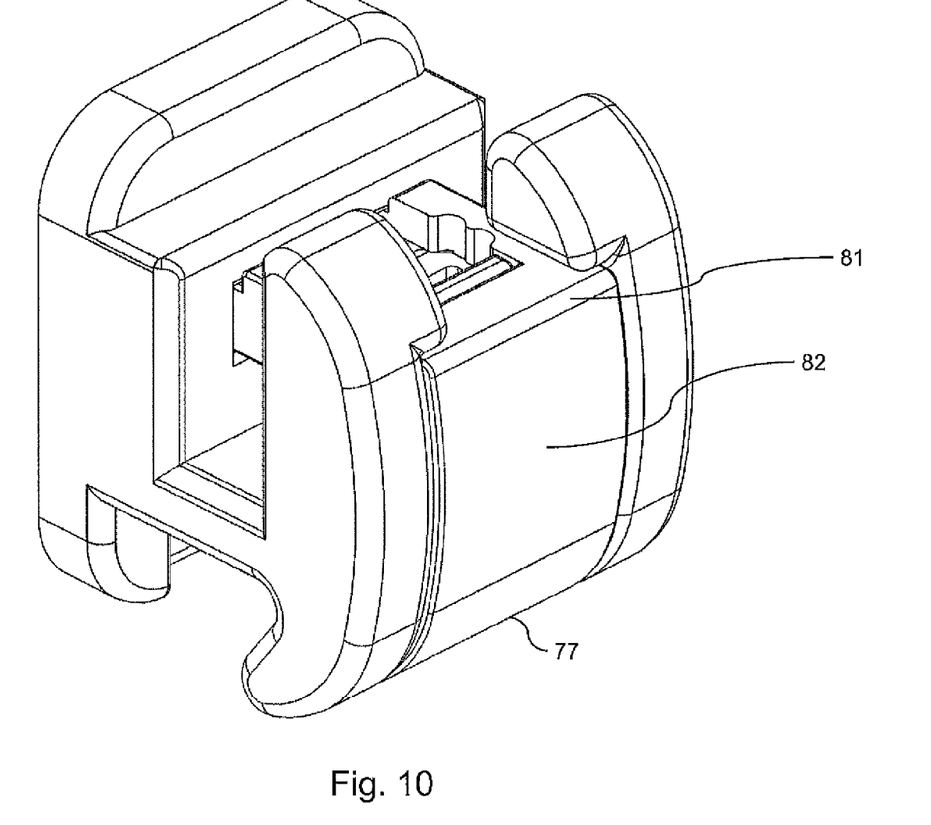
FIG. 10 is a perspective view of an alternative embodiment of the FIG. 1 bracket.

FIG. 10 shows a bracket which differs from the FIG. 1 bracket only in that slide 81 has a smooth outer face 82, without a hole. Spring 14 is accessible and movable as in the FIG. 1 embodiment. Lower lip 77 of slide 14 can be engaged by instrument 71 in order to pull the slide to the open position.

The materials from which the elements of the subject bracket are preferably made would be metal for the body, the slide, and the spring. Other suitable materials for the body include ceramic or an appropriately rigid plastic, and the slide may be made of plastic or a combination of metal and plastic. The spring could be made of plastic or a metal and plastic combination. Of course, the archwire is any standard archwire material used by orthodontists. The body is the most rigid and has no parts which are intended to flex. Because arm 44 of the slide is cantilevered, any metal or relatively rigid plastic (or a combination) that has any ability to flex at all would allow projection 45 to ride up out of slots 46, 47 with reasonable force being applied in the direction of arrows 54, 56. Spring 14 indeed has characteristics of a spring, at least with respect to arm 33, and the sides along opening 31 need to flex only enough to permit projections 22 to move out of a detent 22 or 23 when the spring is moved.

What is claimed is:

1. An orthodontic bracket comprising:
    a body formed with a top opening groove configured to removably receive an archwire;
    a slide configured to fit into a pocket in said body and to be selectively, laterally, slidably engaged in an open position and in a closed position therein, said body and said slide being configured to mutually removably secure the archwire in the groove, said slide is formed with a pair of inwardly projecting arms spaced from each other, there being at least a pair of detents on each said arm, said pair of detents on one said arm facing said pair of detents on the other said arm; and
    an activation spring movably mounted in said slide, said spring is formed with projections on opposite sides, each said projection being configured to removably reside in a selected one of said detents in said slide arms.

2. The bracket according to claim 1, wherein when said spring detents are in one set of facing detents in said slide the bracket is in a passive condition, and when said spring detents are in the other set of facing detents in said slide the bracket is in an active condition.

3. The bracket according to claim 1, wherein said slide is formed with a hole in an outer face thereof for access to said spring.

4. An orthodontic bracket comprising:
    a body formed with a tooth engaging face and a groove to removably receive an archwire, said groove being vertically oriented and generally parallel with said tooth engaging face;
    a slide configured to fit into a pocket in said body in a manner to selectively close the groove to removably secure an archwire in the groove by moving laterally with respect to the tooth engaging face, said slide being formed with detents and a spring member is formed with projections configured to selectively removably engage said detents in a passive stable position and in an active stable position; and
    said spring member coupled to said slide, said slide providing said passive stable position for said spring member and said active stable position for said spring member, said spring member being selectively positioned in the passive or in the active position in said slide.

5. The bracket according to claim 4, wherein said body is formed with at least two spaced detents and said slide is formed with projections configured to selectively reside in said detents to provide at least two stable position of said slide in said body.

6. An orthodontic bracket for selectively holding an archwire in relation to a patient's tooth to which the bracket is adapted to be mounted, the tooth having a linear orientation between its gingival and incisal ends, the bracket comprising:
    a body formed with a groove configured to removably receive the archwire, the groove being oriented in a generally vertical direction so that the archwire is inserted downwardly into the groove in a direction generally parallel with the linear orientation of the tooth in the patient's mouth, said body having:
        a tooth engaging face;
        first and second spaced walls outward from and generally parallel with said tooth engaging face, and a floor connecting said spaced walls, thereby defining three sides of the groove, the outermost of said walls having an opening therethrough;
    a slide configured to move laterally with respect to the tooth and into said opening and providing the top of the groove to thereby confine the archwire when it is inserted into the groove, said body being formed with an open detent and a closed detent, and said slide is formed with a mating tooth configure to securely engage the open detent when in an open position and to removably engage the closed detent when in the closed position; and
    a spring member mounted in said slide selectively movable between a stable passive position and a stable active position, said spring applying force to the archwire when in the active position and not applying force to the archwire when in the passive position.

7. The bracket according to claim 6, wherein said mating tooth is formed at the end of an arm projecting inwardly from said slide.

8. The bracket according to claim 6, wherein said slide is formed with an opening so that said spring is accessible to be moved between the passive position and the active position in said slide.

9. The bracket according to claim 8, wherein said slide has an open position and a closed position with respect to the groove in said body, said spring is movable in said slide when the slide is selectively in the open position and in the closed position.

10. An orthodontic bracket for selectively holding an archwire in relation to a patient's tooth to which the bracket is adapted to be mounted, the tooth having a linear orientation between its gingival and incisal ends, the bracket comprising:
    a body formed with a groove configured to removably receive the archwire, the groove being oriented in a generally vertical direction so that the archwire is inserted downwardly into the groove in a direction generally parallel with the linear orientation of the tooth in the patient's mouth, said body having:
        a tooth engaging face;
        first and second spaced walls outward from and generally parallel with said tooth engaging face, and a floor connecting said spaced walls, thereby defining three sides of the groove, the outermost of said walls having an opening therethrough;

a slide configured to move laterally with respect to the tooth and into said opening and providing the top of the groove to thereby confine the archwire when it is inserted into the groove, said slide being formed with a pair of inwardly projecting arms spaced from each other, there being at least a pair of detents on each said arm, said pair of detents on one said arm facing said pair of detents on the other said arm; and a spring member mounted in said slide selectively movable between a stable passive position and a stable active position, said spring applying force to the archwire when in the active position and not applying force to the archwire when in the passive position, said spring being formed with projections on opposite sides, each said projection being configured to removably reside in a selected one of said detents in said slide arms.

* * * * *